US 11,701,828 B2

United States Patent
Ramos

(10) Patent No.: US 11,701,828 B2
(45) Date of Patent: Jul. 18, 2023

(54) ADDITIVE MANUFACTURING FOR MEDICAL DEVICES

(71) Applicant: Medtronic, Inc., Minneapolis, MN (US)

(72) Inventor: Timothy M. Ramos, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 112 days.

(21) Appl. No.: 17/081,815

(22) Filed: Oct. 27, 2020

(65) Prior Publication Data

US 2021/0122115 A1   Apr. 29, 2021

Related U.S. Application Data

(60) Provisional application No. 62/927,092, filed on Oct. 28, 2019.

(51) Int. Cl.
*B29C 64/336* (2017.01)
*A61M 25/00* (2006.01)
(Continued)

(52) U.S. Cl.
CPC ....... *B29C 64/336* (2017.08); *A61M 25/0009* (2013.01); *B29C 64/118* (2017.08);
(Continued)

(58) Field of Classification Search
CPC ... B29C 64/336; B29C 64/118; B29C 64/295; B33Y 10/00; B33Y 30/00; B33Y 80/00;
(Continued)

(56) References Cited

U.S. PATENT DOCUMENTS

| 2,764,148 A | 9/1956 | Sheldon |
| 3,485,234 A | 12/1969 | Stevens |

(Continued)

FOREIGN PATENT DOCUMENTS

| CA | 2998126 | 10/2018 |
| EP | 1053039 | 11/2000 |

(Continued)

OTHER PUBLICATIONS

Dilberoglu et al., "Current trends and research opportunities in hybrid additive manufacturing", The International Journal of Advanced Manufacturing Technology, 113, 2021, pp. 623-648.

(Continued)

*Primary Examiner* — Joseph S Del Sole
*Assistant Examiner* — Jamel M Nelson
(74) *Attorney, Agent, or Firm* — Mueting Raasch Group

(57) ABSTRACT

An additive manufacturing system may include a heating cartridge defining an interior volume and at least one filament port. The system may include a heating element thermally coupled to the heating cartridge to heat the interior volume. The system may also include a filament handling system to feed at least one filament through the at least one filament port. The system may include a substrate handling system having at least a head stock. The system may include a controller configured to initiate or control movement of a substrate relative to the heating cartridge to apply a jacket to the substrate.

25 Claims, 18 Drawing Sheets

(51) Int. Cl.
    *B29C 64/118*     (2017.01)
    *B29C 64/295*     (2017.01)
    *B33Y 30/00*     (2015.01)
    *B33Y 80/00*     (2015.01)
    *B33Y 10/00*     (2015.01)
    *B29L 31/00*     (2006.01)

(52) U.S. Cl.
    CPC ............ *B29C 64/295* (2017.08); *B33Y 10/00* (2014.12); *B33Y 30/00* (2014.12); *B33Y 80/00* (2014.12); *A61M 2207/10* (2013.01); *B29L 2031/7542* (2013.01)

(58) Field of Classification Search
    CPC ........... A61M 25/0009; A61M 2207/10; B29L 2031/7542
    See application file for complete search history.

(56) References Cited

U.S. PATENT DOCUMENTS

| | | | |
|---|---|---|---|
| 5,871,475 | A | 2/1999 | Frassica |
| 6,591,472 | B1 | 7/2003 | Noone et al. |
| 7,306,617 | B2 | 12/2007 | Majercak |
| 7,833,218 | B2 | 11/2010 | Lunn et al. |
| 7,909,033 | B2 | 3/2011 | Faram |
| 8,118,827 | B2 | 2/2012 | Duerig et al. |
| 8,509,916 | B2 | 8/2013 | Byrd et al. |
| 9,002,496 | B2 | 4/2015 | Elsey |
| 9,043,191 | B2 | 5/2015 | Grady et al. |
| 9,974,887 | B2 | 5/2018 | Eversull et al. |
| 10,254,499 | B1 | 4/2019 | Cohen et al. |
| 10,327,862 | B2 | 6/2019 | Lubinski |
| 10,442,175 | B2 | 10/2019 | Schlachter |
| 10,548,355 | B2 | 2/2020 | Volpis et al. |
| 10,610,666 | B2 | 4/2020 | Stern |
| 10,751,507 | B2 | 8/2020 | Palmer et al. |
| 2004/0002677 | A1 | 1/2004 | Gentsler |
| 2007/0005041 | A1 | 1/2007 | Frassica et al. |
| 2007/0060863 | A1 | 3/2007 | Goeken et al. |
| 2008/0262472 | A1 | 10/2008 | Lunn et al. |
| 2012/0149985 | A1 | 6/2012 | Frassica et al. |
| 2014/0284838 | A1 | 9/2014 | Pfeffer et al. |
| 2014/0361460 | A1 | 12/2014 | Mark |
| 2015/0217517 | A1 | 8/2015 | Karpas et al. |
| 2016/0096323 | A1 | 4/2016 | Fry et al. |
| 2016/0101262 | A1 | 4/2016 | Root et al. |
| 2016/0184233 | A1 | 6/2016 | Palomar-Moreno et al. |
| 2016/0207220 | A1 | 7/2016 | Hack et al. |
| 2016/0303347 | A1* | 10/2016 | Porter ................... B29C 48/157 |
| 2017/0189553 | A1 | 7/2017 | Hunter |
| 2017/0259506 | A1 | 9/2017 | Ho et al. |
| 2018/0036123 | A1 | 2/2018 | Costello |
| 2018/0065320 | A1 | 3/2018 | Tyler |
| 2018/0117855 | A1 | 5/2018 | Girou et al. |
| 2018/0141274 | A1 | 5/2018 | Fink et al. |
| 2018/0168687 | A1 | 6/2018 | Drake et al. |
| 2018/0254099 | A1 | 9/2018 | Beydoun et al. |
| 2018/0289925 | A1 | 10/2018 | Palmer et al. |
| 2018/0370117 | A1 | 12/2018 | Gardiner et al. |
| 2019/0002625 | A1 | 1/2019 | Jiang et al. |
| 2019/0209080 | A1 | 7/2019 | Gullotti et al. |
| 2019/0240456 | A1 | 8/2019 | Pokorny et al. |
| 2019/0351185 | A1 | 11/2019 | Assouline et al. |
| 2019/0375149 | A1* | 12/2019 | Limem ................. B33Y 80/00 |
| 2020/0080237 | A1 | 3/2020 | Vogt et al. |
| 2020/0093505 | A1 | 3/2020 | Sinelnikov et al. |
| 2021/0122115 | A1 | 4/2021 | Ramos |
| 2021/0236767 | A1 | 8/2021 | Warnock, Jr. et al. |
| 2021/0298730 | A1 | 9/2021 | Baxter et al. |
| 2022/0226636 | A1 | 1/2022 | Rassat et al. |
| 2022/0032002 | A1 | 2/2022 | Baxter et al. |
| 2022/0032003 | A1 | 2/2022 | Baxter et al. |
| 2022/0032537 | A1 | 2/2022 | Baxter et al. |

FOREIGN PATENT DOCUMENTS

| | | |
|---|---|---|
| KR | 101863192 | 6/2018 |
| WO | 2014/172545 | 10/2014 |
| WO | 2016/168505 | 10/2016 |
| WO | 2019/070899 | 4/2019 |

OTHER PUBLICATIONS

International Search Report and Written Opinion from PCT Application No. PCT/US2021/024640 dated Sep. 13, 2021, 17 pages.
International Search Report and Written Opinion from PCT/US2021/043795 dated Oct. 20, 2021, 14 pages.
International Search Report and Written Opinion from PCT/US2021/043794 dated Nov. 2021. 11 pages.
International Search Report and Written Opinion from PCT Application No. PCT/US2022/012966, dated Jun. 13, 2022, 19 pages.
International Search Report and Written Opinion from PCT/US2021/043914 dated Dec. 20, 2021, 18 pages.
Gardeski et al., U.S. Appl. No. 17/215,842, filed Mar. 29, 2021.
Gardeski et al., U.S. Appl. No. 63/001,832, filed Mar. 30, 2020.
Warnock Jr. et al., U.S. Appl. No. 17/162,101, filed Jan. 29, 2021.
Warnock Jr. et al., U.S. Appl. No. 62/970,561, filed Feb. 5, 2020.
Ascend Medical Technologies, "Design Guidelines for 3D X-Fusion Technology", ascendmedtech.com/design-guidelines, retrieved Oct. 25, 2019, 3 pages.
Ascend Medical Technologies, "Engineering Capabilities", ascendmedtech.com/design-guidelines, retrieved Oct. 25, 2019, 7 pages.
International Preliminary Report on Patentability for PCT Application No. PCT/US2021/024640 dated Oct. 13, 2022, 10 pages.

\* cited by examiner

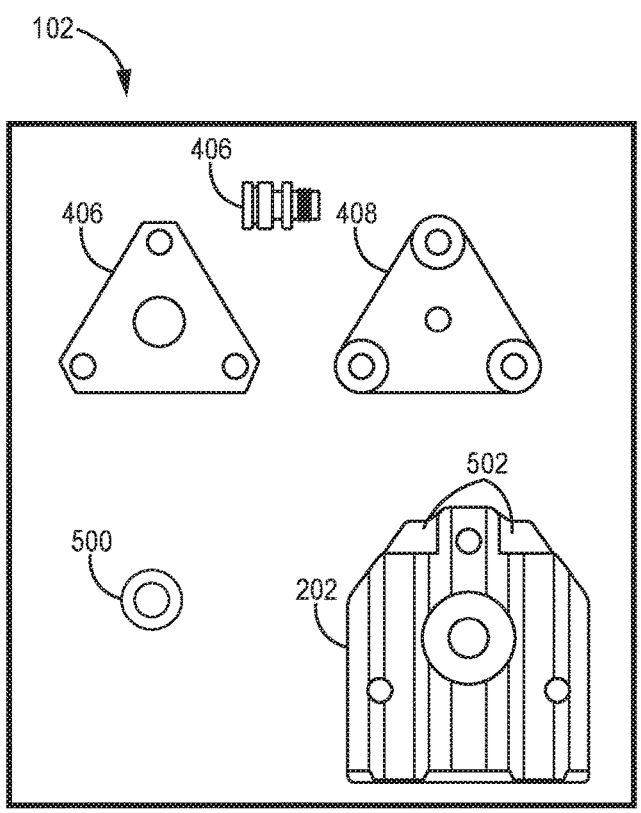 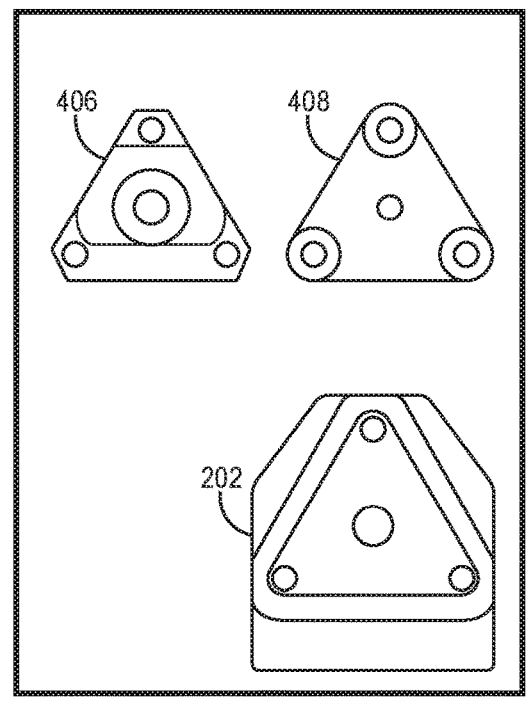
FIG. 12A  FIG. 12B

ADDITIVE MANUFACTURING FOR MEDICAL DEVICES

The present application claims the benefit of U.S. Provisional Application No. 62/927,092, filed Oct. 28, 2019, which is incorporated herein by reference in its entirety.

The disclosure generally relates to medical devices and, in particular, additive manufacturing of medical devices, such as catheters and implantable stimulation leads.

A number of medical devices, such as medical catheters, are designed to be navigated through tortuous paths in a human body, such as through a patient's vasculature. Medical catheters and leads are commonly used to access vascular and other locations within a body and to perform various functions at those locations, for example, delivery catheters may be used to deliver medical devices, such as implantable medical leads. Medical catheters and leads may be designed to be sufficiently flexible to move through turns, or curves, in the vasculature yet sufficiently stiff, or resilient, to be pushed through the vasculature. In many cases, such as those involving cardiovascular vessels, the route to the treatment or deployment site may be tortuous and may present conflicting design considerations that may require compromises between dimensions, flexibilities, material selection, operational controls and the like. These contrasting properties can present challenges in designing and manufacturing catheters. Existing manufacturing processes, such as conventional extrusion, may also limit options in designing and manufacturing catheters.

SUMMARY

The techniques of the present disclosure generally relate to additive manufacturing of medical devices, such as catheters and leads, that allows for the use of a wider range of filament or pellet materials to create a wide range of resulting catheter or lead characteristics. For example, a wider variety of hardness levels can be achieved compared to existing techniques to produce catheters, catheter components, or implantable devices. In particular, the present techniques allow for feeding soft filaments at high feed forces during additive manufacturing, or three-dimensional (3D) printing. Additionally, the present techniques may facilitate new catheters and implantable devices.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIGS. 12A-B are images of proximal and distal sides of examples of components of a heating cartridge in an unassembled state for use with, for example, the heating cartridge in the additive manufacturing system of FIG. 1.

DETAILED DESCRIPTION

Figure 1:
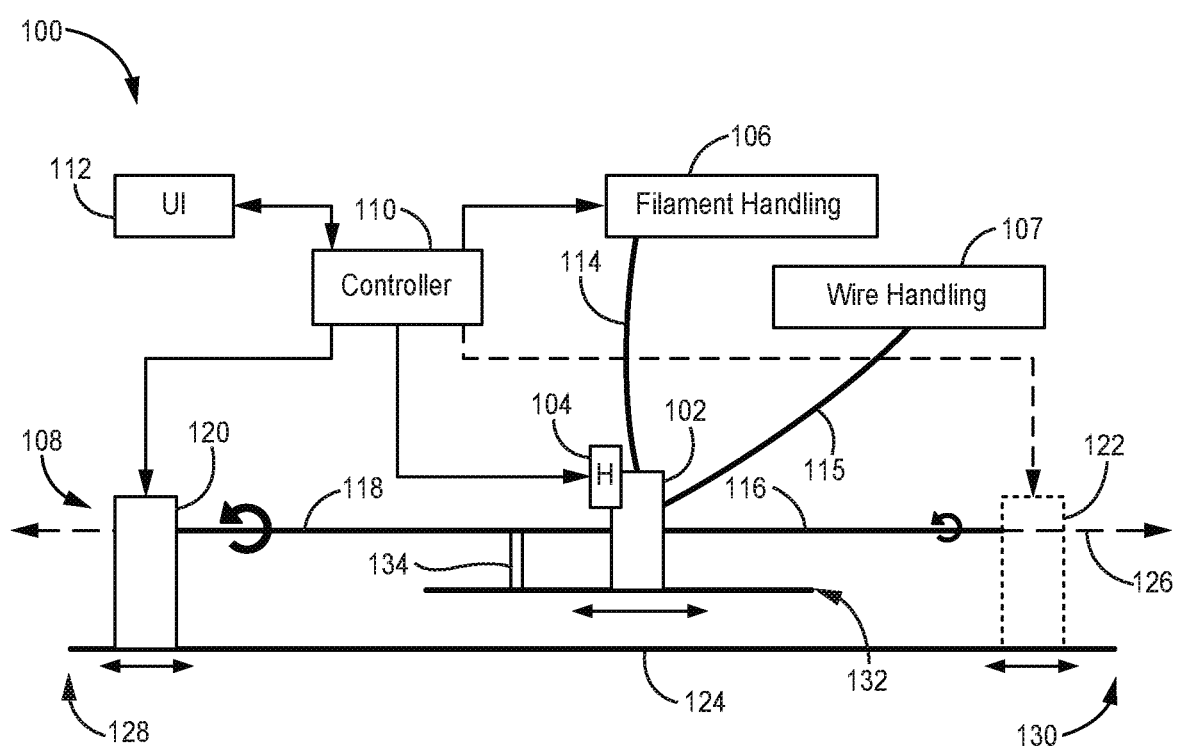
FIG. 1 is a conceptual diagram that illustrates one example of an additive manufacturing system according to the present disclosure.

The present disclosure generally provides additive manufacturing systems and methods for medical devices, such as catheters and leads, that allows for the use of a wider range of filament or pellet materials to create a wide range of resulting catheter or lead characteristics. For example, a wider variety of hardness levels can be achieved compared to existing techniques to produce catheters, catheter components, or implantable devices. Additive manufacturing may also be described as three-dimensional (3D) printing. The additive manufacturing systems of the present disclosure allow feeding soft filaments at high feed forces, which may facilitate a wider range of operating conditions for prototyping or manufacturing. Further, new catheters and implantable dev ices may be facilitated by the wider range filament materials and operating conditions.

The systems and methods described herein allow for 3D printing of medical devices, which may facilitate constructions with unique combinations of properties which may enable new treatments. Unique catheter handling properties may be achieved by combining materials in ways not traditionally combined in catheter manufacturing and may include materials that are new to catheter construction. In addition, 3D printing may allow for including other accessories, such as steering capability via pull wires, in a space efficient manner.

In some embodiments, the systems and methods described herein may facilitate concurrently depositing multiple standard geometry 3D printing filament or pellet resin on a surface in an up to 360 degree radial plane via a variable shape die, to produce various surface profiles, onto the surface of a part moving in multiple planes including radially.

In some embodiments, the systems and methods described herein may facilitate concurrently depositing multiple standard geometry 3D printing filament resin at varying thickness over a surface via varying filament feed rate, die size, and substrate velocity.

In some embodiments, the systems and methods described herein may facilitate utilizing multiple in-line pinch rollers to increase push-ability of flexible standard geometry 3D printing filament resin.

In some embodiments, the systems and methods described herein may facilitate concurrently depositing multiple and varying stiffness standard geometry 3D printing filament resin at varying blend ratio to produce varying flex modulus and color of deposited material.

In some embodiments, the systems and methods described herein may facilitate utilizing a lumen, which may be sized for standard geometry 3D printing filament, made particularly of polytetrafluoroethylene (PTFE) liner tube for lubricity and TORLON polyamide-imide for advanced thermal properties, and designed for a single PTFE tube to channel filament from pinch rollers into a heater cartridge, with heat break and heat sink characteristics provided by the TORLON, resulting in an increase in filament "push-ability."

In some embodiments, the systems and methods described herein may facilitate utilizing an alignment guide to support and align a moving part while depositing standard geometry 3D printing filament resin on the part's surface.

In some embodiments, the systems and methods described herein may facilitate utilizing tooling to assemble input and output dies in a concentric manner for the process of depositing multiple standard geometry 3D printing filament resin.

In some embodiments, the systems and methods described herein may facilitate utilizing input and output die geometries to facilitate various resin deposition profiles and also concurrently added materials, such as wires, etc., embedded within the deposited resin, which may be used with standard geometry 3D printing filament resin.

In some embodiments, the systems and methods described herein may facilitate utilizing variably tuned pinch roller pressure, used on standard geometry 3D printing filament, to optimize grip and push-ability per a given filament durometer.

As used herein, the term "or" refers to an inclusive definition, for example, to mean "and/or" unless its context of usage clearly dictates otherwise. The term "and/or" refers to one or all of the listed elements or a combination of at least two of the listed elements.

As used herein, the phrases "at least one of" and "one or more of" followed by a list of elements refers to one or more of any of the elements listed or any combination of one or more of the elements listed.

As used herein, the terms "coupled" or "connected" refer to at least two elements being attached to each other either directly or indirectly. An indirect coupling may include one or more other elements between the at least two elements being attached. Either term may be modified by "operatively" and "operably," which may be used interchangeably, to describe that the coupling or connection is configured to allow the components to interact to carry out described or otherwise known functionality. For example, a controller may be operably coupled to a resistive heating element to allow the controller to provide an electrical current to the heating element.

As used herein, any term related to position or orientation, such as "proximal," "distal," "end," "outer," "inner," and the like, refers to a relative position and does not limit the absolute orientation of an embodiment unless its context of usage clearly dictates otherwise.

All scientific and technical terms used herein have meanings commonly used in the art unless otherwise specified. The definitions provided herein are to facilitate understanding of certain terms used frequently herein and are not meant to limit the scope of the present disclosure.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 shows one example of an additive manufacturing system 100 according to the present disclosure. The system 100 may be configured and used to produce a catheter, catheter component, lead, or subassembly. The system 100 may use or include consumable filament materials or pellet form resins having a wide variety of hardness levels. The system 100 may be configured to operate a wide variety of process conditions to produce catheters, catheter components, leads, or subassemblies using filaments or pellet form resins of various hardness levels. In general, the system 100 defines a distal region 128, or distal end, and a proximal region 130, or proximal end. The system 100 may include a platform 124 including a rigid frame to support one or more components of the system.

As shown in the illustrated embodiment, the system 100 may include one or more components, such as a heating cartridge 102, a heating element 104, a filament handling system 106, an optional wire handling system 107, a substrate handling system 108, a controller 110, and a user interface 112. The filament handling system 106 may be operably coupled to the heating cartridge 102. The filament handling system 106 may provide one or more filaments 114 to the heating cartridge 102. The optional wire handling system 107 may be used to provide one or more wires 115 to the heating cartridge 102. The heating element 104 may be operably coupled, or thermally coupled, to the heating cartridge 102. The heating element 104 may provide heat to melt filament material in the heating cartridge 102 from the one or more filaments 114 provided by the filament handling system 106. The optional wires 115 may not be melted by the heating cartridge 102. The substrate handling system 108 may be operably coupled to the heating cartridge 102. The substrate handling system 108 may provide a substrate 116 that extends through the heating cartridge. Melted filament material located in the heating cartridge 102 may be applied to the substrate 116. The substrate 116 or the heating cartridge 102 may be translated or rotated relative to one another by the substrate handling system 108. The substrate handling system 108 may be used to move the substrate 116 or the heating cartridge 102 relative to one another to cover the substrate 116 with the melted filament material to form a jacket 118. The optional wires 115 may be incorporated into the jacket 118 (e.g., molded into, bedded within, etc.).

The substrate 116 may also be described as a mandrel or rod. The jacket 118 may be formed or deposited around the substrate 116. In some embodiments, the jacket 118 may be formed concentrically around the substrate 116. In one example, the jacket 118 is formed concentrically and centered around the substrate 116.

Figure 13:
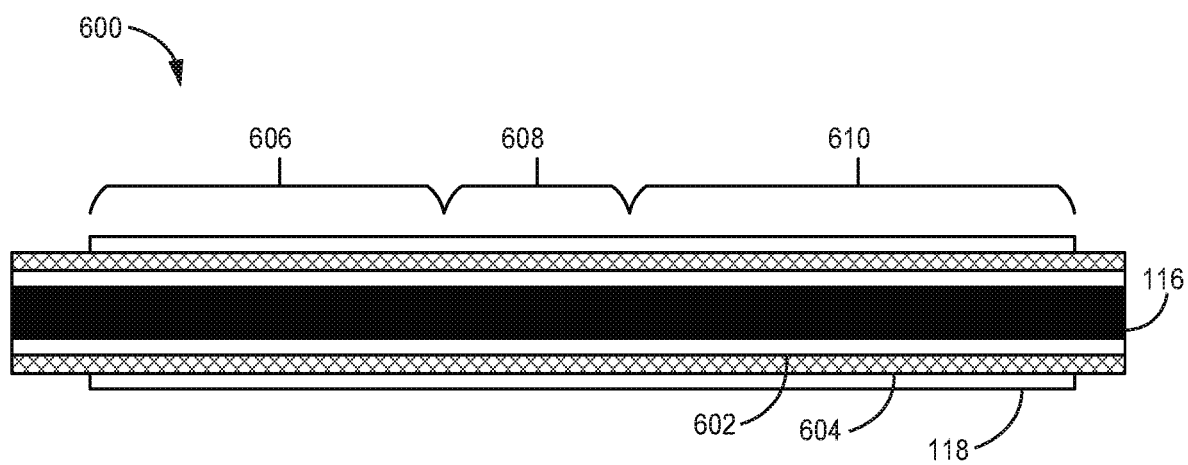
FIG. 13 is a conceptual diagram of that illustrates one example of a catheter that may be manufactured, before the substrate is removed, using the additive manufacturing system of FIG. 1.

When the system 100 is used to make a catheter or catheter component, the jacket 118 may be described as a catheter jacket. Some or all of the substrate 116 may be removed or separated from the jacket 118 and the remaining structure coupled to the jacket may form the catheter or catheter component, such as a sheath. One example of a catheter that may be formed by the system 100 is shown in FIG. 13.

The substrate 116 may be formed of any suitable material capable of allowing melted filament material to be formed thereon. In some embodiments, the substrate 116 is formed of a material that melts at a higher temperature than any of the filaments 114. One example of a material that may be used to form the substrate 116 includes stainless steel.

The controller 110 may be operably coupled to one or more of the heating element 104, the filament handling system 106, the substrate handling system 108, and the user interface 112. The controller 110 may activate, or initiate or otherwise "turn on," the heating element 104 to provide heat to the heating cartridge 102 to melt the filament material located therein. Further, the controller 110 may control or command one or more motors or actuators of various portions of the system 100. Furthermore, the controller 110 may control one or more motors or actuators the filament handling system 106 to provide one or more filaments 114. Further, the controller 110 may control one or more motors or actuators of the substrate handling system 108 to move one or both of the heating cartridge 102 or the substrate 116 relative to one another. Further still, the controller 110 may send or receive data to the user interface 112, for example, to display information or to receive user commands. Control of the components operably coupled to the controller 110 may be determined based on user commands received by the user interface 112. In some embodiments, the user commands may be provided in the form of a machine-readable code or coding language.

Any suitable implementation may be used to provide the substrate handling system 108. In some embodiments, the substrate handling system 108 may include one or more of a head stock 120, an optional tail stock 122, and one or more motors coupled to or included in the head stock or tail stock. One or both of the head stock 120 and the tail stock 122 may be coupled to the platform 124. A stock may be defined as a structure that holds or secures the substrate 116 during formation of the jacket 118. The head stock 120 is defined as the stock closest to the end of the substrate 116 where formation of the jacket 118 begins in the formation process. In the illustrated embodiment, the jacket 118 is shown proximal to the head stock 120 and distal to the heating cartridge 102.

When the substrate 116 is secured by one or both stocks 120, 122, the substrate is generally positioned to pass through a substrate channel defined by the heating cartridge 102. One or both stocks 120, 122 may include a clamp or other securing mechanism to selectively hold the substrate 116. Such a clamp may be operably coupled to a substrate motor. In some embodiments, the substrate motor may be used to control opening and closing of the clamp. In some embodiments, the substrate motor may be used to rotate the substrate 116 in a clockwise or counterclockwise direction about a longitudinal axis 126. A translation motor may be operably coupled between a stock 120, 122 and the platform 124. In some embodiments, the translation motor may be used to translate the stock 120, 122 in a longitudinal direction along the longitudinal axis 126. In some embodiments, the translation motor also may be used to translate the stock 120, 122 in a lateral direction different than the longitudinal axis 126. The lateral direction may be oriented substantially orthogonal, or perpendicular, to the longitudinal axis 126.

In some embodiments, the substrate handling system 108 may be configured to move the head stock 120 at least in a longitudinal direction (for example, parallel to the longitudinal axis 126) relative to the platform 124. The substrate 116 may be fed through the substrate channel of the heating cartridge 102 by movement of the head stock 120 relative to the platform 124. A distal portion of the substrate 116 may be clamped into the head stock 120. The head stock 120 may be positioned close to the heating cartridge 102 at the beginning of the jacket formation process. The head stock 120 may move distally away from the heating cartridge 102, for example in a direction parallel to the longitudinal axis 126. In other words, the head stock 120 may move toward the distal region 128 of the system 100 while pulling the secured substrate 116 through the heating cartridge 102. As the substrate 116 passes through the heating cartridge 102, melted filament material from the filament 114 may be formed or deposited onto the substrate 116 to form the jacket 118. The heating cartridge 102 may be stationary relative to the platform 124. In some embodiments, the tail stock 122 may be omitted.

In some embodiments, the substrate handling system 108 may be configured to move the heating cartridge 102 at least in a longitudinal direction (along the longitudinal axis 126) relative to the platform 124. The substrate 116 may be fed through the substrate channel of the heating cartridge 102. A distal portion of the substrate 116 may be clamped into the head stock 120. A proximal portion of the substrate 116 may be clamped into the tail stock 122. In one example, the heating cartridge 102 may be positioned relatively close to the head stock 120 at the beginning of the jacket formation process. The heating cartridge 102 may move proximally away from the head stock 120. The heating cartridge 102 may move toward the proximal region 130 of the system 100. As the heating cartridge 102 passes over the substrate 116, melted filament material may be deposited onto the substrate 116 to form a jacket. The head stock 120 and the tail stock 122 may be stationary relative to the platform 124. In another example, the heating cartridge 102 may start near the tail stock 122 and move toward the distal region 128.

One or more motors of the substrate handling system 108 may be used to rotate one or both of the substrate 116 and the heating cartridge 102 relative to one another. In some embodiments, only the substrate 116 may be rotated about the longitudinal axis 126. In some embodiments, only the heating cartridge 102 may be rotated about the longitudinal axis 126. In some embodiments, both the substrate 116 and the heating cartridge 102 may be rotated about the longitudinal axis 126.

The heating cartridge 102 may be part of a subassembly 132. The subassembly 132 may be coupled to the platform 124. In some embodiments, one or more motors of the substrate handling system 108 may be coupled between subassembly 132 and the platform 124 to translate or rotate the subassembly 132, including the heating cartridge 102, relative to the platform 124 or the substrate 116. In some embodiments, one or more motors of the substrate handling system 108 may be coupled between a frame of the subassembly 132 and the heating cartridge 102 to translate or rotate the heating cartridge relative to the platform 124.

In some embodiments, the substrate 116 may be rotated about the longitudinal axis 126 relative to the heating cartridge 102 to facilitate forming certain structures of the jacket. In one example, the substrate 116 may be rotated by one or both of the head stock 120 and the tail stock 122 of the substrate handling system 108. In another example, the heating cartridge 102 or subassembly 132 may be rotated by the substrate handling system 108.

The system 100 may include one or more concentricity guides 134. The concentricity guide 134 may facilitate adjustments to the concentricity of the jacket around the substrate 116 before or after the substrate passes through the heating cartridge 102. The concentricity guide 134 may be longitudinally spaced from the heating cartridge 102. In some embodiments, the spacing may be greater than or equal to 1, 2, 3, 4, or 5 cm. The spacing may be sufficient to allow the jacket 118 to cool down and no longer be deformable. In some embodiments, one or more concentricity guides 134 may be positioned distal to the heating cartridge 102 and to engage the jacket 118. In some embodiments, one or more concentricity guides 134 may be positioned proximal to the heating cartridge 102 to engage the substrate 116. The concentricity guide 134 may mitigate drooping of the substrate 116 and may mitigate susceptibility to eccentricity in the alignment of the stock 120, 122 and the heating cartridge 102.

Any suitable implementation may be used to provide the filament handling system 106. One or more filaments 114 may be loaded into the filament handling system 106. For example, filaments 114 may be provided in the form of wound coils. Filaments 114 may be fed to the heating cartridge 102 by the filament handling system 106. In some embodiments, the filament handling system 106 may include one, two, or more pinch rollers to engage the one or more filaments 114. In some embodiments, the filament handling system 106 may include one or more motors. The one or more motors may be coupled to the one or more pinch rollers to control rotation of the pinch rollers. The force exerted by the motors onto the pinch rollers and thus onto the one or more filaments 114 may be controlled by the controller 110.

In some embodiments, the filament handling system 106 may be configured to feed the filaments 114 including at least a first filament and a second filament. The jacket 118 may be formed from the material of one or both of the filaments 114. The filament handling system 106 may be capable of selectively feeding the first filament and the second filament. For example, one motor may feed the first filament and another motor may feed the second filament. Each of the motors may be independently controlled by the controller 110. Selective, or independent, control of the feeds may allow for the same or different feed forces to be applied to each of the filaments 114.

The filaments 114 may be made of any suitable material, such as polyethylene, PEBAX elastomer (commercially available from Arkema S.A. of Colombes, France), nylon 12, polyurethane, polyester, liquid silicone rubber (LSR), or PTFE.

The filaments 114 may have any suitable Shore durometer. In some embodiments, the filaments 114 may have, or define, a Shore durometer suitable for use in a catheter. In some embodiments, the filaments 114 have a Shore durometer of at least 25 A and up to 90 A. In some embodiments, the filaments 114 have a Shore durometer of at least 25 D and up to 80 D.

In some embodiments, the filament handling system 106 may provide a soft filament as one of the filaments 114. In some embodiments, a soft filament may have a Shore durometer less than or equal to 90 A, 80 A, 70 A, 80 D, 72 D, 70 D, 60 D, 50 D, 40 D, or 35 D.

In some embodiments, the filament handling system 106 may provide a hard filament and a soft filament having a Shore durometer less than the soft filament. In some embodiments, the soft filament has a Shore durometer that is 10 D, 20 D, 30 D, 35 D, or 40 D less than a Shore durometer of the hard filament.

The system 100 may be configured to provide a jacket 118 between the Shore durometers of a hard filament and a soft filament. In some embodiments, the filament handling system 106 may provide a hard filament having a Shore durometer equal to 72 D and a soft filament having a Shore durometer equal to 35 D. The system 100 may be capable of providing a jacket 118 having a Shore durometer that is equal to or greater than 35 D and less than or equal to 72 D.

The system 100 may be configured to provide a jacket 118 having, or defining, segments with different Shore durometers. In some embodiments, the system 100 may be capable of providing a jacket 118 having one or more of a 35 D segment, a 40 D segment, 55 D segment, and a 72 D segment.

The filaments 114 may have any suitable width or diameter. In some embodiments, the filaments 114 have a width or diameter of 1.75 mm. In some embodiments, the filaments 114 have a width or diameter of less than or equal to 1.75, 1.5, 1.25, 1, 0.75, or 0.5 mm.

Segments may have uniform or non-uniform Shore durometers. The system 100 may be configured to provide jacket 118 having one or more segments with non-uniform Shore durometers. In some embodiments, the jacket 118 may include continuous transitions between at least two different Shore durometers, for example, as shown in FIG. 13.

The controller 110 may be configured to change a feeding force applied to one or more of the filaments 114 to change a ratio of material in the jacket over a longitudinal distance. By varying the feeding force, the system 100 may provide different Shore durometer segments in a jacket 118, whether uniform or non-uniform. In one example, sharp transitions between uniform segments may be provided by stopping or slowing longitudinal movement while continuously, or discretely with a large step, changing the feeding force of one filament relative to another filament of the substrate 116 relative to the heating cartridge 102. In another example, gradual transitions between segments may be provided by continuously, or discretely with small steps, changing the feeding force of one filament relative to another filament while longitudinally moving the substrate 116 relative to the heating cartridge 102.

The system 100 may be configured to provide a jacket 118 having varying thicknesses. In some embodiments, the controller 110 may be configured to vary one or more parameters, for example, at least one of: a longitudinal speed of the substrate 116 relative to the heating cartridge 102, a feeding force applied to one or more filaments 114, and an amount of heat provided by the heating element 104. Varying one or more of these parameters during formation of the jacket 118 may be used to change a thickness of the jacket over a longitudinal distance. In some embodiments, the controller 110 may be configured to vary one or more of these parameters in conjunction with using a particular heating cartridge (see FIG. 18).

The one or more wires 115 provided by the wire handling system 107 may be introduced in any suitable manner. In some embodiments, the wires 115 may be attached to the substrate 116 and pulled by movement of the substrate. One example of a wire is a pull wire that may be used to steer the catheter produced by the system 100. In some embodiments, a particularly shaped heating cartridge may be used to accommodate one or more wires 115 (see FIGS. 15-16).

Any suitable type of heating element 104 may be used. In some embodiments, the heating element 104 may be a resistive-type heating element, which may provide heat in response to an electrical current. Other types of heating elements that may be used for the heating element 104 include a radio frequency (RF) or ultrasonic-type heating element. The heating element 104 may be capable of providing heat sufficient to melt the filaments 114. In some embodiments, the heating element 104 may heat the filaments 114 to greater than or equal to 235, 240, 250, or 260 degrees Celsius. In general, the one or more heating elements 104 may be used to heat the filaments 114 to any suitable melting temperature known to one of ordinary skill in the art having the benefit of this disclosure.

Any suitable user interface 112 may be used to communicate with the controller 110. Non-limiting examples of user interfaces 112 include one or more of a stationary or portable computer, a monitor or other display, a touchscreen, a keyboard, a mouse, a tablet, a phone, a knob, a switch, a button, and the like. In some embodiments, the user interface 112 may allow the user to input direct commands to or to enter code to program operations of the controller 110.

In one example, a program may include various command lines, such as:

M567 P0 E 0:1
G1 X100 E50 F200
M567 P0 E 0.25:0.75
G1 X100 E50 F100
M567 P0 E 0.5:0.5
G1 X100 E50 F60
M567 P0 E 0.75:.25
G1 X100 E50 F50
M567 P09 E 1:0
G1 X100 E50 F50

Such a program may "print" the following catheter jacket segments:
a) 100 mm segment with a flow rate 50 at speed 200. Mixture ratio 0% material 1 and 100% material 2.
b) 100 mm segment with flow rate 50 at speed 100. Mixture ratio 25% material 1 and 75% material 2.
c) 100 mm segment with flow rate 50 at speed 60. Mixture ratio 0% material 1 and 50% material 2.
d) 100 mm segment with flow rate 50 at speed 50. Mixture ratio 75% material 1 and 25% material 2.
e) 100 mm segment with flow rate 50 at speed 50. Mixture ratio 100% material 1 and 0% material 2.

As used herein, the term "flow rate" refers to a filament feed rate according to any suitable unit of measurement. In some embodiments, material 1 may be 35 D PEBAX and material 2 may be 72 D PEBAX. In general, as the mixture ratio transitions to a softer durometer material, the overall feed rate (F ###) may decrease. Decreasing the feed rate may reduce the tendency for the softer durometer material to jam. Certain techniques described herein may reduce the need to decrease the overall feed rate. The flow rate command (E ###) may directly affect the wall thickness of the printed catheter jacket.

Figure 2:
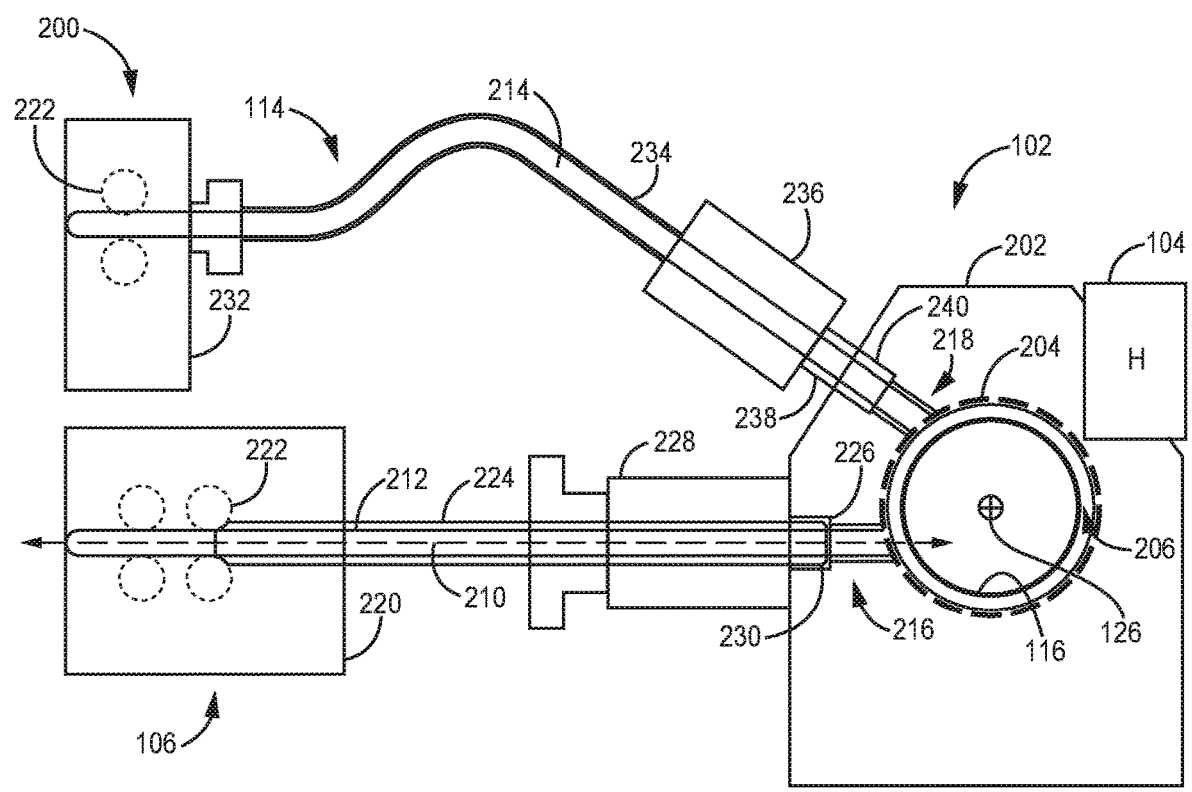
FIG. 2 is a conceptual diagram that illustrates one example of an additive manufacturing apparatus for use with, for example, the additive manufacturing system of FIG. 1.

FIG. 2 shows one example of an additive manufacturing apparatus 200 of the additive manufacturing system 100 in an end view along the longitudinal axis 126, which is illustrated as a circle and cross. More detail of some components of the additive manufacturing system 100 are shown, such as the heating cartridge 102 and the filament handling system 106.

The heating cartridge 102 may include a heating block 202 at least partially defining an interior volume 204. The interior volume 204 may be heated by the heating element 104. The heating element 104 may be thermally coupled to the heating block 202 to melt filament material in the interior volume 204. In general the system 100 may be configured to melt any portion of the filaments 114 in the interior volume 204. The heating element 104 may be disposed in an exposed or exterior volume 502 (FIG. 12A) defined in the heating block 202. The heating element 104 may be positioned proximate to or adjacent to the interior volume 204. In some embodiments, one, two, three, or more heating elements 104 may be thermally coupled to the heating block 202.

The heating block 202 may allow the substrate 116, which may be an elongate substrate or member, to pass through the heating block. The substrate 116 may be able to extend, or pass, through the interior volume 204. The substrate channel 206 defined by the heating cartridge 102 may extend through the interior volume 204. The substrate channel 206 may extend in a same or similar direction as the substrate 116. The substrate channel 206 may extend along the longitudinal axis 126.

A width or diameter of the interior volume 204 is larger than a width or diameter of the substrate 116. The width or diameter of the interior volume 204 or the substrate 116 is defined in a lateral direction, which may be orthogonal to the longitudinal axis 126. In one example, the lateral direction may be defined along a lateral axis 210. In some embodiments, the clearance between the substrate 116 and interior volume 204 is relatively small to facilitate changes in composition of filament material used to form the jacket 118 (FIG. 1) around the substrate 116.

The portion of the interior volume 204 around the substrate 116 may receive a flow of melted filament material from the filaments 114. When more than one filament material is provided to the interior volume 204, the filament materials may flow and blend, or mix, around the substrate 116.

In the illustrated embodiment, the filaments 114 includes a first filament 212 and a second filament 214. The first filament 212 may be provided into the interior volume 204 through a first filament port 216 at least partially defined by the heating block 202. The second filament 214 may be provided into the interior volume 204 through a second filament port 218 at least partially defined by the heating block 202. Each filament port 216, 218 may be at least partially defined by the heating block 202. Each filament port 216, 218 may be in fluid communication with the interior volume 204.

The filaments 114 may be delivered to the interior volume 204 in the same or different manners. In the illustrated embodiment, the first filament 212 is delivered to the interior volume 204 in a different manner than the second filament 214.

The filament handling system 106 may include a first handling subassembly 220. The first handling subassembly 220 may deliver the first filament 212 to the interior volume 204. The first handling subassembly 220 may include one or more pinch rollers 222. Each of the one or more pinch rollers 222 may be operably coupled to a motor. Any suitable number of pinch rollers 222 may be used. As illustrated, the first handling subassembly 220 may include two sets of pinch rollers 222. Pinch rollers 222 may be used to apply a motive force to the first filament 212 to move the first filament, for example, toward the interior volume 204.

The heating cartridge 102 may include a first guide sheath 224. The first guide sheath 224 may extend between the filament handling system 106 and the interior volume 204. The first guide sheath 224 may be coupled to the heating block 202. The first guide sheath 224 may extend into the first filament port 216 from an exterior of the heating block 202. The first guide sheath 224 may define a lumen in fluid communication with the interior volume 204. An inner width or diameter of the lumen may be defined to be greater than a width or diameter of the first filament 212. The first filament 212 may extend through the first guide sheath 224 from the pinch rollers 222 of the first handling subassembly 220 to the first filament port 216 and extend distally past the first guide sheath 224 into the interior volume 204.

As used herein with respect to the filaments 114, the term "distal" refers to a direction closer to the interior volume 204 and the term "proximal" refers to a direction closer to the filament handling system 106.

In some embodiments, a proximal end of the first guide sheath 224 may terminate proximate to one of the pinch rollers 222. A distal end of the first guide sheath 224 may terminate at a shoulder 226 defined by the first filament port 216. A distal portion or distal end of the first guide sheath 224 may be positioned proximate to or adjacent to the interior volume 204.

The inner width or diameter of the lumen of the first guide sheath 224 may be defined to be substantially the same or equal to an inner width or diameter of the first filament port 216, such as a smallest inner width or diameter of the first filament port. In other words, an inner surface of the first guide sheath 224 may be flush with an inner surface of the first filament port 216.

In some embodiments, the heating cartridge 102 may include a support element 228. The support element 228 may be coupled to the first guide sheath 224. The first guide sheath 224 may extend through a lumen defined by the support element 228. The support element 228 may be proximate to the heating block 202. In the illustrated embodiment, the support element 228 is coupled to the heating block 202. The support element 228 may include a coupling protrusion configured to be mechanically coupled to a coupling receptacle 230 defined by the first filament port 216. In some embodiments, the coupling receptacle 230 may define threads and the coupling protrusion of the support element 228 may define complementary threads.

The coupling receptacle 230 may terminate at the shoulder 226 of the first filament port 216. The coupling protrusion of the support element 228 may be designed to terminate at the shoulder 226. In some embodiments, a distal end of the support element 228 and the distal end of the first guide sheath 224 may engage the shoulder 226. In other embodiments, the distal end of the support element 228 may engage the shoulder 226 and the distal end of the first guide sheath 224 may engage a second shoulder (not shown) defined by the first filament port 216 distal to the shoulder 226.

When the first filament port 216 defines one shoulder, the first filament port 216 may define at least two different inner widths or diameters. The larger inner width or diameter may be sized to thread the support element 228 and the smaller inner width or diameter may be sized to match the inner width or diameter of the first guide sheath 224.

When the second filament port 218 defines two shoulders, the first filament port 216 may define at least three different inner widths or diameters. The largest inner width or diameter may be sized to thread the support element 228. The intermediate inner width or diameter may be sized to receive a distal portion of the first guide sheath 224. The smallest inner width or diameter may be sized to match the inner width or diameter of the first guide sheath 224.

The filament handling system 106 may include a second handling subassembly 232. The second handling subassembly 232 may deliver the second filament 214 to the interior volume 204. The second handling subassembly 232 may include one or more pinch rollers 222. Each of the one or more pinch rollers 222 may be operably coupled to a motor. Any suitable number of pinch rollers 222 may be used. As illustrated, the second handling subassembly 232 may include one set of pinch rollers 222. Pinch rollers 222 may be used to apply a motive force to the second filament 214.

The heating cartridge 102 may include one or more of a second guide sheath 234, a heat sink 236, and a heat break 238. The second guide sheath 234 may extend at least between the second handling subassembly 232 and the heat sink 236. The second guide sheath 234 may be coupled to the heat sink. The second guide sheath 234 may be coupled to the second handling subassembly 232. The heat sink 236 may be coupled to the heat break 238. The heat break 238 may be coupled to the heat block 202. The heat break 238 may extend into the second filament port 218 from an exterior of the heating block 202.

The second guide sheath 234 may define a lumen in fluid communication with the interior volume 204. The second filament 214 may extend through the second guide sheath 234 from the second handling subassembly 232 to the heat sink 236, through the heat sink 236, through the heat break, and through the second filament port 218. In some embodiments, the second guide sheath 234 may extend to the pinch rollers 22 in the second handling subassembly 232. In some embodiments, the second guide sheath 234 may extend at least partially into the heat sink 236.

The heat break 238 may be proximate to the heating block 202. The heat break 238 may be positioned between the heat sink 236 and the heating block 202. The heat break 238 may include a coupling protrusion configured to mechanically couple to a coupling receptacle 240 defined by the second filament port 218. In some embodiments, the coupling receptacle 240 may define threads and the coupling protrusion of the heat break 238 may define complementary threads. The second filament port 218 may include one or more shoulders such as those described with respect to the first filament port 216, except that the second filament port 218 may not be configured to receive the second guide sheath 234. The inner width or diameter of the support element 228 may be larger than the inner width or diameter of the heat break 238, for example, to accommodate the outer width or diameter of the first guide sheath 224. In other embodiments, the second filament port 218 may be configured to receive the second guide sheath 234 in a similar manner to the first filament port 216 receiving the first guide sheath 224.

Any suitable material may be used to make the guide sheaths 224, 234. In some embodiments, one or both guide sheaths 224, 234 may include a synthetic fluoropolymer. One or both guide sheaths 224, 234 may include polytetrafluoroethylene (PTFE). Another suitable material may include an ultra-high molecular weight polyethylene (UHMWPE).

Any suitable material may be used to make the support element 228. In some embodiments, the support element 228 may be a thermal insulator. The support element 228 may include a thermoplastic. The support element 228 may be made of a polyamide-imide, such as a TORLON polyamide-imide (commercially available from McMaster-Carr Supply Co. of Elmhurst, Illinois). Other suitable materials may include liquid-crystal polymer, polyaryletherketone (PAEK), polyphenylene sulfide, and polysulfone.

The support element 228 may provide mechanical support to the first guide sheath 224. The support element 228 may include a substantially rigid material. In some embodiments, the support element 228 include a material having a higher durometer than material used to make the first guide sheath 224.

Any suitable material may be used to make the heat sink 236. The heat sink 236 may include a high thermal conductivity material. In some embodiments, the heat sink 236 includes aluminum.

Any suitable material may be used to make the heat break 238. The heat break 238 may include a low thermal conductivity material. In some embodiments, the heat break 238 includes titanium. The heat break 238 may include a necked portion to reduce the amount of material between a proximal portion and a distal portion of the heat break. The necked portion may facilitate a reduced thermal conductivity between the proximal portion and the distal portion of the heat break 238.

In general, use of the apparatus 200 may facilitate using softer filaments at high feed forces and pressures, which tend to compress the soft filament and may result in jamming. Using higher feed forces and pressures may allow for a greater range of process conditions and may provide a consistent jacket around the substrate. In particular, use of the first guide sheath 224 extending at least partially into the first filament port 216 may facilitate the use of softer filament and greater "push-ability." Additionally, or alternatively, the use of the support element 228 may also facilitate the use of softer filament and greater "push-ability."

Figure 3:
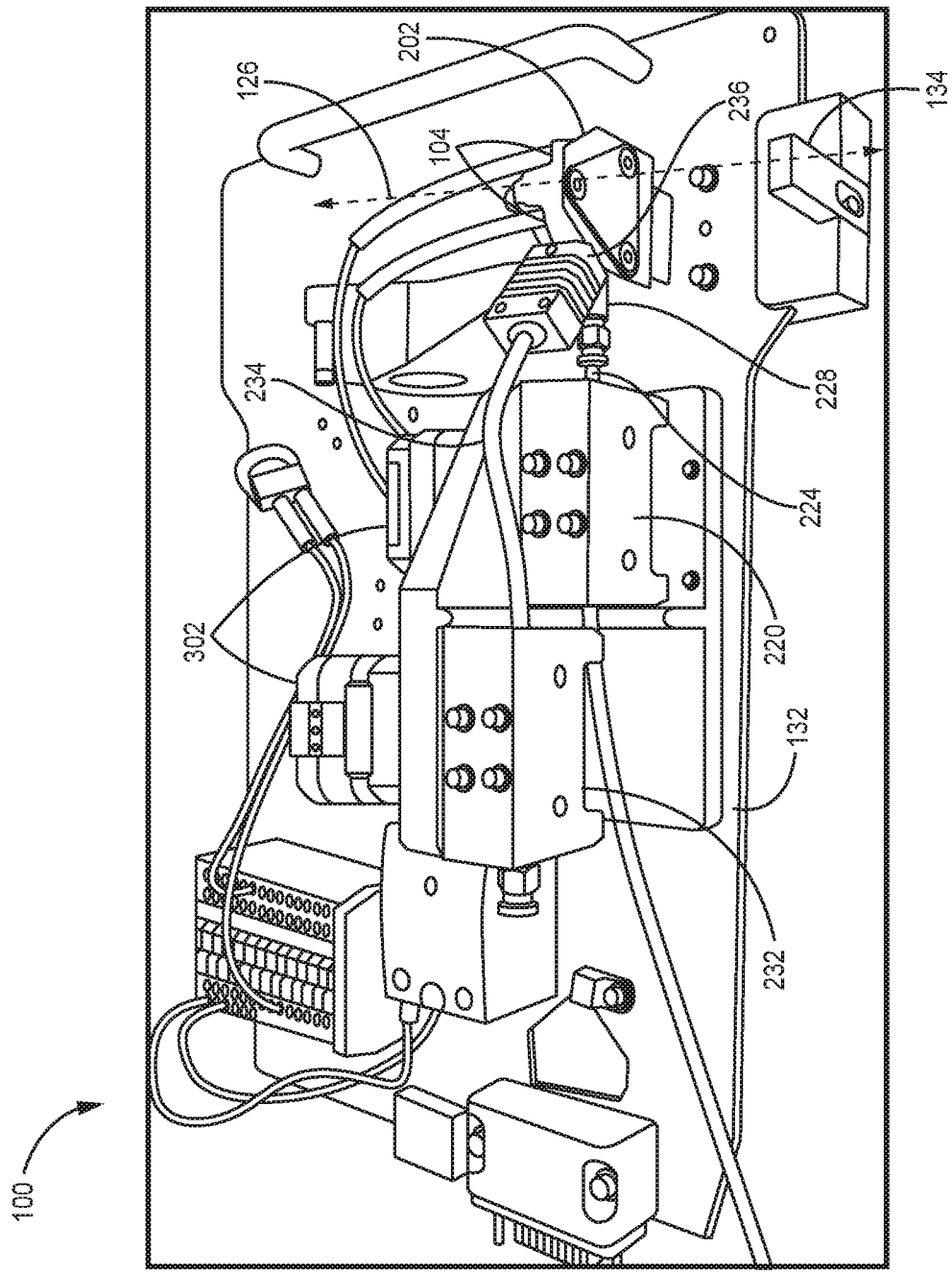
FIG. 3 is an image of one example of a subassembly for use with, for example, the additive manufacturing system of FIG. 1.

FIG. 3 is an overhead perspective image showing one example of the subassembly 132. As illustrated, the subassembly 132 includes the concentricity guide 134 aligned with heating block 202 along longitudinal axis 126, two heating elements 104 coupled to the heating block, the support element 228 coupled to the heating block, the first guide sheath 224 coupled to the support element 228, the first handling subassembly 220 including a motor 302 and coupled to the first guide sheath, the heat sink 236 coupled to the second guide sheath 234, and the second handling subassembly 232 including another motor 302 coupled to the second guide sheath. In some embodiments, one, two, three, or more heating elements 104 may be used.

Figure 4:
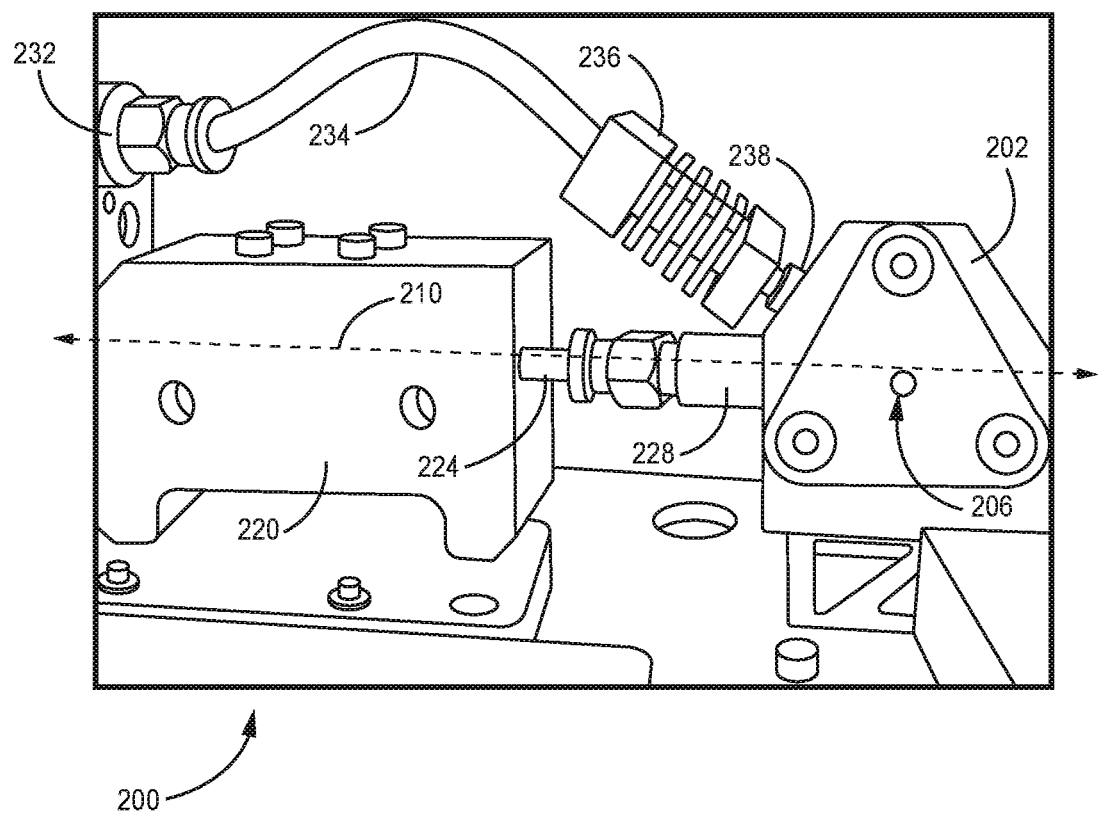
FIG. 4 is an image of one example of the additive manufacturing apparatus of FIG. 2.

FIG. 4 is an end perspective image showing one example of the additive manufacturing apparatus 200. As illustrated, the apparatus 200 includes the heating block 202 at least partially defining the substrate channel 206, a first guide sheath 224 extending along the lateral axis 210 coupled to the first handling subassembly 220, the support element 228 coupled to the first guide sheath and to the heating block, the second guide sheath 234 coupled to the second handling subassembly 232, the heat sink 236 coupled to the second guide sheath, and the heat break 238 coupled to the heat sink and the heating block.

Figure 5:
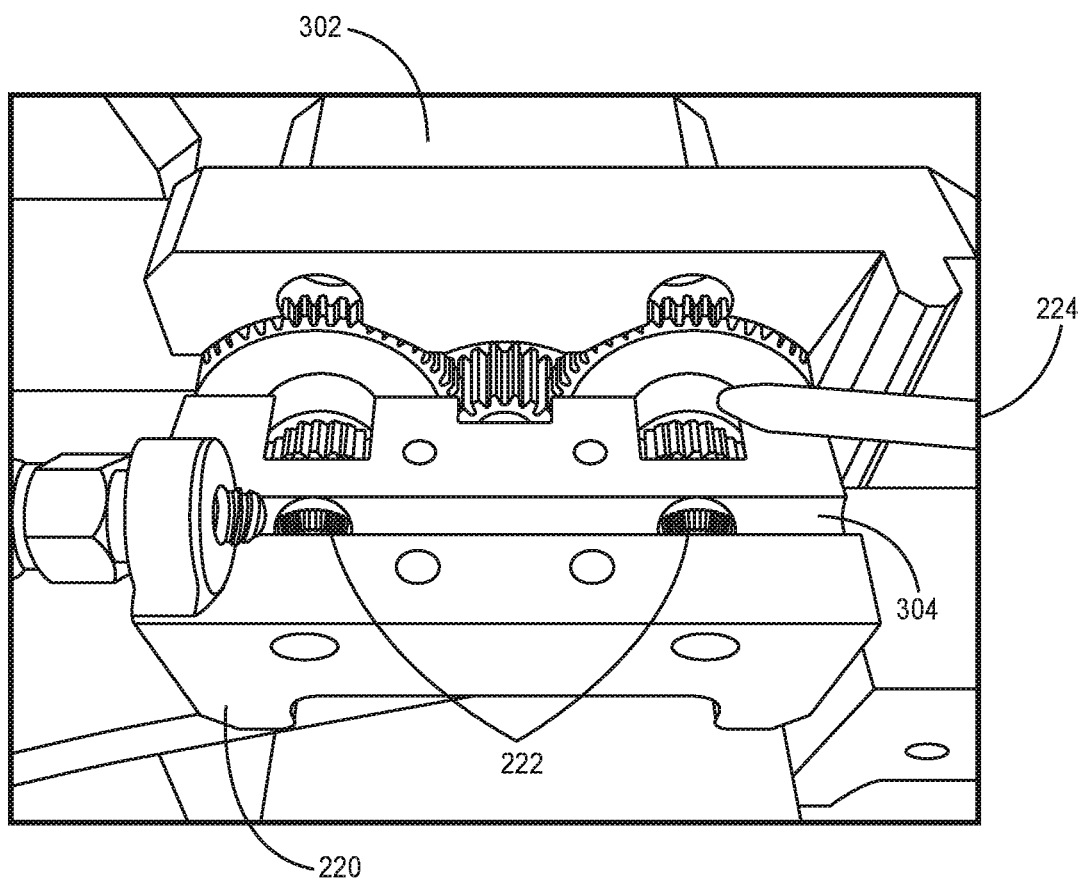
FIG. 5 is an image of one example of a first handling subassembly with a top portion removed for use with, for example, the additive manufacturing system of FIG. 1.

FIG. 5 is an overhead perspective image showing one example of the first handling subassembly 220 with a top portion removed. The first handling subassembly 220 includes two sets of pinch rollers 222 coupled to one of the motors 302. The first handling subassembly 220 forms a channel 304 configured to receive the first filament 212 (FIG. 2). A proximal end of the first guide sheath 224 extends into the channel 304 of the first handling subassembly and terminates proximate to the distal pinch roller 222. In particular, the first guide sheath 224 terminates just distal to the most distal pinch roller 222.

Figure 6:
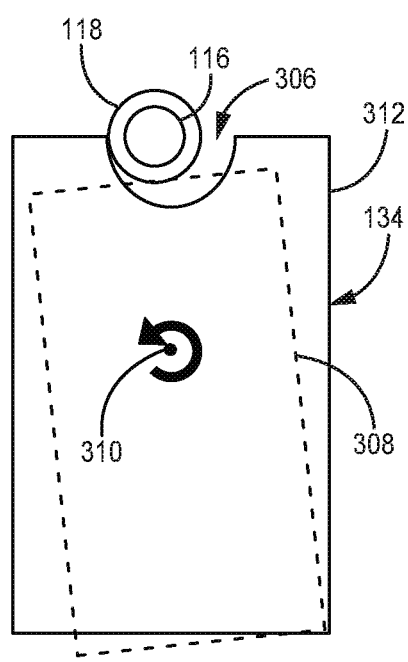
FIG. 6 is a conceptual diagram that illustrates one example of a concentricity guide for use with, for example, the additive manufacturing system of FIG. 1.

FIG. 6 shows one example of the concentricity guide 134. In some embodiments, the concentricity guide 134 may facilitate supporting the substrate 116 or the jacket 118 around the substrate 116. In some embodiments, the concentricity guide 134 may facilitate centering the jacket 118 around the substrate 116. The concentricity guide 134 may act upon (e.g., be in contact with, support, etc.) the jacket 118 after leaving the heating cartridge 102 (FIG. 2) and the jacket material is cooled down and no longer deformable.

The concentricity guide 134 may include a stationary member 312 that defines a channel 306. The channel 306 may be sized to receive the substrate 116 or the substrate 116 covered by the jacket 118. The concentricity guide 134 may include an adjustable member 308. The adjustable member 308 may be configured to laterally position (e.g., left or right within the channel 306 as shown) the substrate 116 or the jacket 118 covering the substrate 116 relative to the channel 306. The adjustable member 308 may be adjustable coupled to the stationary member 312. In some embodiments, the adjustable member 308 may be rotatably coupled to the stationary member 312.

Figure 7:
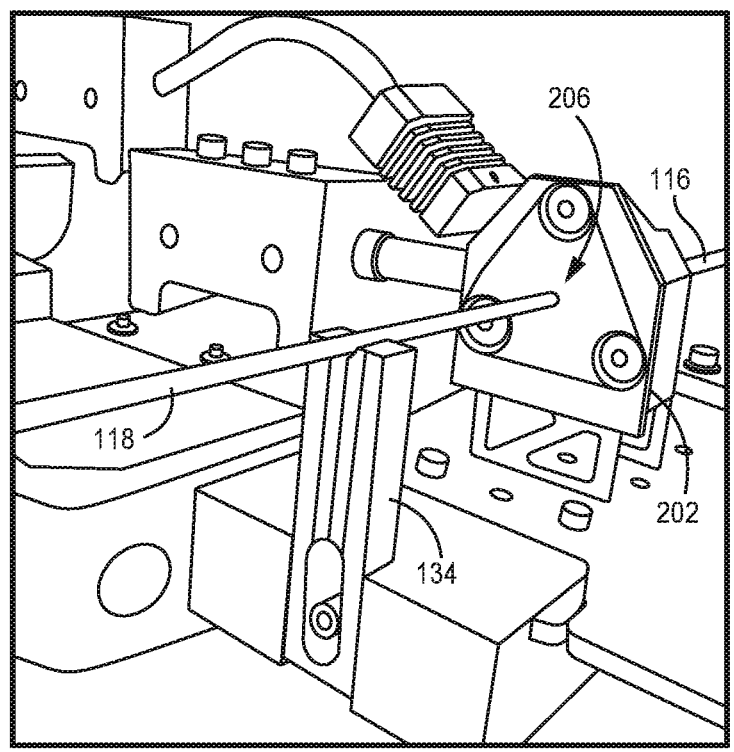
FIG. 7 is an image of one example of a concentricity guide and a heating block for use with, for example, the additive manufacturing system of FIG. 1.

FIG. 7 is a side perspective image showing one example of the concentricity guide 134 in use with the heating block 202. As illustrated, the substrate 116 extends through the substrate channel 206 of the heating block 202 and is coated with the jacket 118. The concentricity guide 134 (without the adjustable member) is shown supporting the jacket 118 around the substrate 116.

Figure 8:
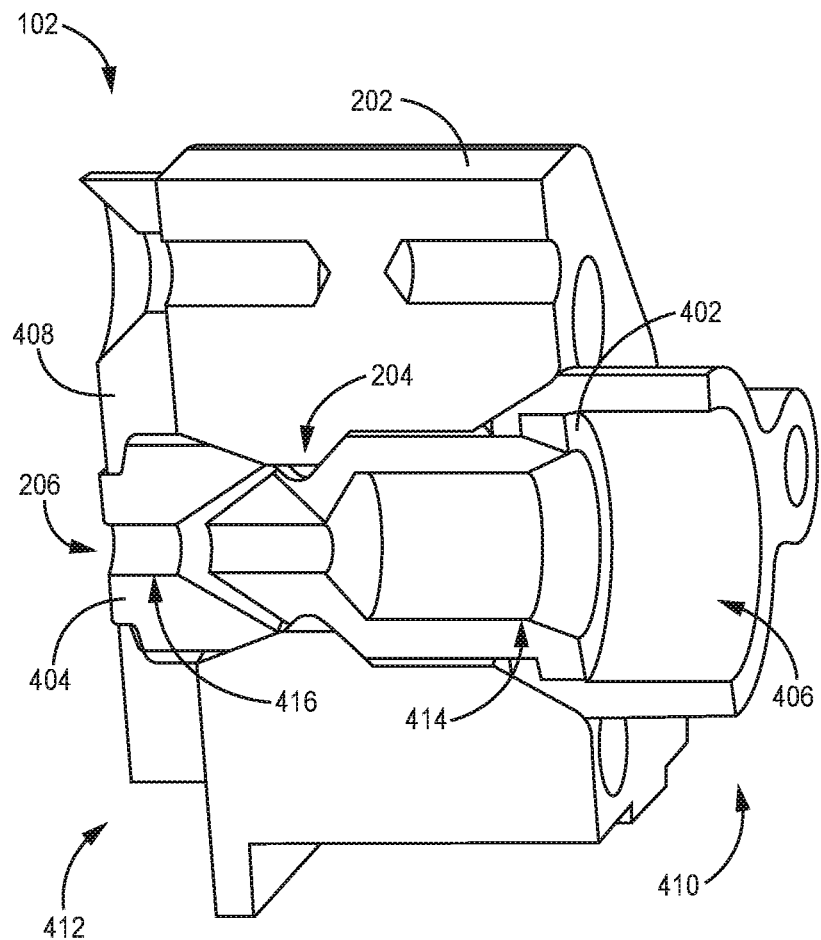
FIG. 8 is a conceptual diagram that illustrates one example of a heating cartridge for use with, for example, the additive manufacturing system of FIG.1.

FIG. 8 shows a partial cross-sectional side view of one example of the heating cartridge 102. The heating cartridge 102 or the heating block 202 may extend from a proximal side 410 to a distal side 412. In some embodiments, the heating cartridge 102 may include one or more of the heating block 202, an inlet die 402 coupled to the proximal side 410 of the heating block, an outlet die 404 coupled to the distal side 412 of the heating block, a proximal retaining plate 406 to facilitate retaining the inlet die adjacent to the heating block, and a distal retaining plate 408 to facilitate retaining the outlet die adjacent to the heating block.

The inlet die 402 and the outlet die 404 may be retained in any suitable manner. In the illustrated embodiment, the outlet die 404 may be retained by a distal shoulder of the distal retaining plate 408. In some embodiments, the inlet die 402 may be retained by the proximal retaining plate 406 between a distal shoulder of the proximal retaining plate 406 and a fastener 500 (see FIG. 12A), such as a nut with a lumen extending through, which may be threaded to the retaining plate to engage a proximal surface of the inlet die. The retaining plates 406, 408 may be fastened to the heating block 202 in any suitable manner.

The inlet die 402 may at least partially define a substrate inlet port 414. The outlet die 404 may at least partially define a substrate outlet port 416.

The inlet die 402 may at least partially define the interior volume 204. The outlet die 404 may at least partially define the interior volume 204. In some embodiments, an exterior surface of the inlet die 402, an interior surface of the outlet die 404, and an interior surface of the heating block 202 may cooperatively define the interior volume 204.

The substrate channel 206 may be described as extending from the proximal side 410 to the distal side 412 of the heating cartridge 102, or vice versa. The substrate channel 206 may extend through the interior volume 204. As shown, the substrate channel 206 may extend through one or more of the proximal retaining plate 406, the inlet die 402, the heating block 202, the outlet die 404, and the distal retaining plate 408.

Figure 9:
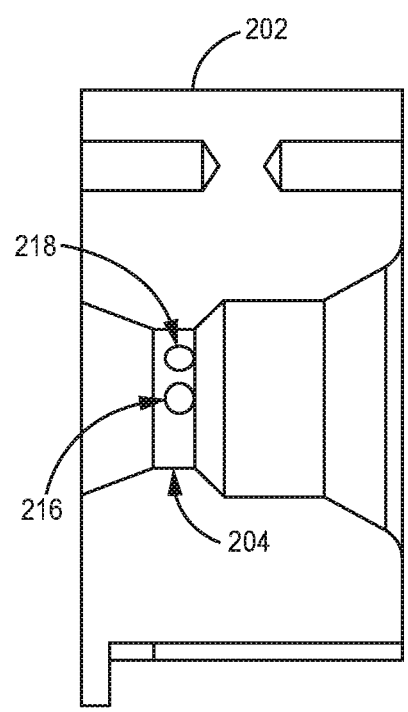
FIG. 9 is a conceptual diagram that illustrates one example of the heating cartridge of FIG. 8 in a different view.

FIG. 9 shows the heating block 202 used in the heating cartridge 102 shown in FIG. 8. With the dies removed, an orifice of the first filament port 216 and an orifice of the second filament port 218 connecting the filament ports to the interior volume 204 are visible.

Figure 10:
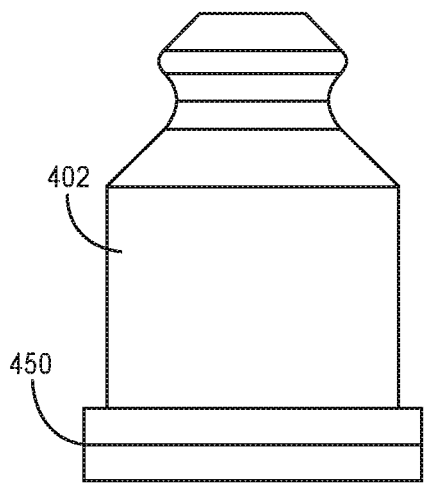
FIG. 10 is a conceptual diagram that illustrates one example of an inlet die for use with, for example, the heating cartridge in the additive manufacturing system of FIG. 1.
Figure 11:
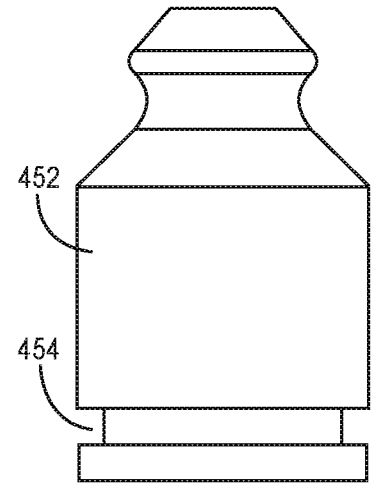
FIG. 11 is a conceptual diagram that illustrates another example of an inlet die for use with, for example, the heating cartridge in the additive manufacturing system of FIG. 1.

FIG. 10 shows the inlet die 402 having a shoulder 450, which may be retained between the proximal retaining plate 406 (FIG. 8) and the fastener 500 (FIG. 12A). FIG. 11 shows an alternative inlet die 452 having a groove 454, which may be used to engage a clip, such as an E-clip or radial retaining ring.

FIGS. 12A-B show proximal and distal sides of various components of the heating cartridge 102 in an unassembled state. FIG. 12A shows the proximal sides, whereas FIG. 12B shows the distal sides.

As illustrated, the heating cartridge 102 includes the proximal retaining plate 406, the distal retaining plate 408, the heating block, and the fastener 500, which may be threaded into an aperture in the proximal side of the proximal retaining plate 406.

A side view of the heat break 238 is shown in FIG. 12A. As can be seen, the heat break 238 may include a necked portion and a coupling protrusion (threaded).

In the illustrated embodiment, the heating block 202 includes two exterior volumes 502, or notches or receptacles. The exterior volumes 502 may be used to receive a heating element 104 (FIG. 1).

FIG. 13 shows one example of a catheter 600 that may be manufactured using the system 100 before the substrate 116 is removed. The substrate 116 may include a lubricious coating on its exterior surface to facilitate removal. The lubricious coating may extend around the circumference of the substrate 116. One example of a lubricious coating is a PTFE coating.

The substrate 116 may be covered with a liner 602, such as a PTFE layer. The liner 602 may be placed over the lubricious coating. The liner 602 may extend around the circumference of the substrate 116.

The liner 602 may be covered with a braid 604, such as a stainless-steel braid layer. The braid 604 may be placed over the liner 602. The braid 604 may extend around the circumference of the liner 602. The braid 604 may be porous.

The jacket 118 may be applied to the braid 604. When the jacket 118 is formed, the liner 602 may adhere to the jacket 118 through pores in the braid 604.

In the illustrated embodiments, the catheter 600 includes a first segment 606, a second segment 608, and a third segment 610. Each segment 606, 608, 610 may have different durometers. In some embodiments, the first segment 606 may have a high durometer, the third segment 610 may have a low durometer, and the second segment 608 may have a continuously varying durometer in a longitudinal direction between the durometers of the first and third segments. For example, the first segment 606 may have a Shore durometer equal to 72 D, the third segment 610 may have a Shore durometer equal to 35 D, and the second segment 608 may have a Shore durometer that gradually changes from 72 D to 35 D over its length.

Figure 14:
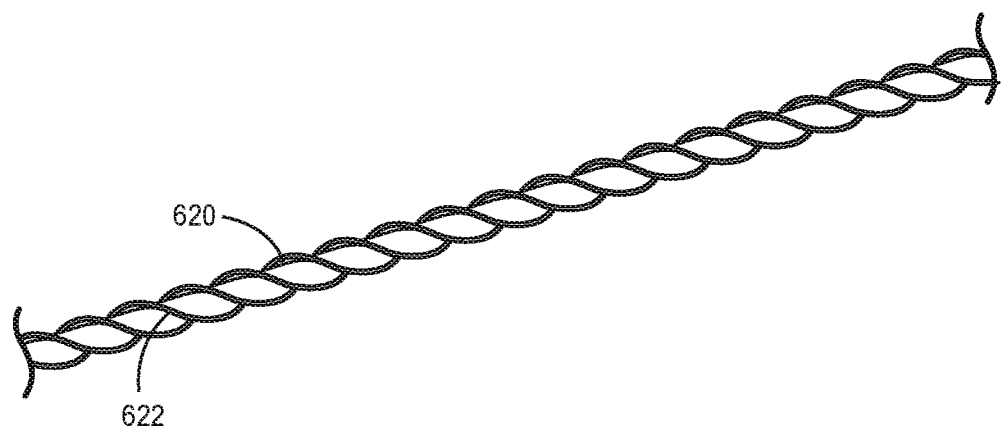
FIG. 14 is an image of one example of a catheter that may be manufactured using the additive manufacturing system of FIG. 1.

FIG. 14 shows one example of a jacket 620 that may be formed using the system 100. The jacket 620 may include one or more protrusions 622 forming at least part of the exterior surface of the jacket 620. As illustrated, the protrusions 622 may be spiral or helical along the length of the jacket 620. The spiral protrusions 622 may be used, for example, as an auger to pull the catheter through tight, tortuous anatomy when rotating and pushing on the catheter no longer advance the catheter to the target site.

The system 100 may, for example, rotate the substrate 116 (FIG. 1) or the heating cartridge 102 (FIG. 1) relative to one another while translating the substrate relative to the heating cartridge. The jacket 620 may be formed using particular inlet or outlet dies (see FIGS. 15-16).

Figure 15:
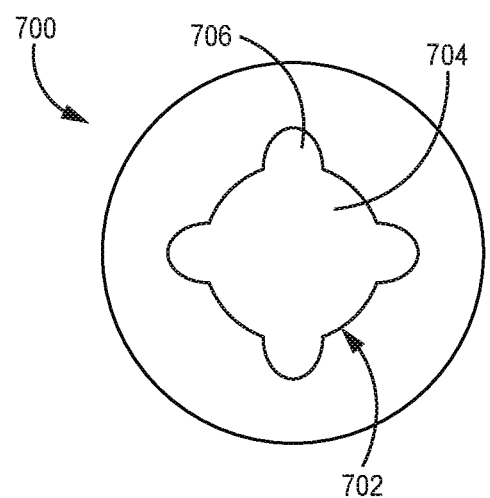
FIG. 15 is a conceptual diagram that illustrates one example of an inlet or outlet die that may be used, for example, in the heating cartridge in the additive manufacturing system of FIG. 1.

FIG. 15 shows an end view of one example of an inlet or outlet die 700 that may be used in the heating cartridge 102 (FIG. 1). The die 700 may define a substrate inlet or outlet port 702. The port 702 may define a main region 704 and one, two, three, four, or more cutouts 706, or cutout regions. In the illustrated embodiment, the port 702 defines four cutouts 706.

When the interior cross-sectional shape die 700 is used in an outlet die, the jacket formed by the heating cartridge 102 may include a number of protrusions corresponding to the number of cutouts 706 used in the die 700. For example, the illustrated die 700 would produce four protrusions on the jacket.

Figure 16:
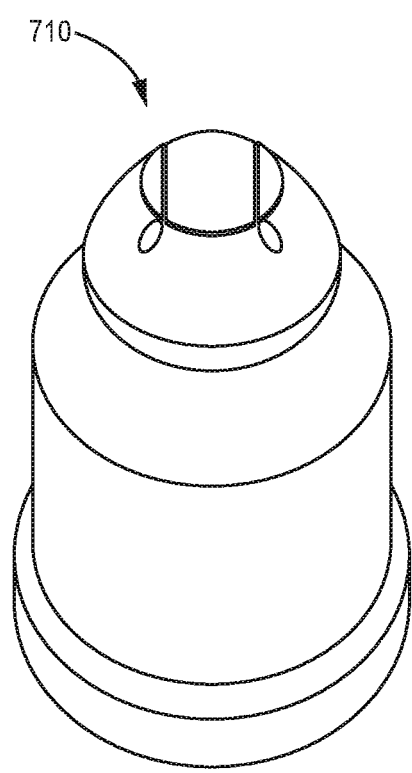
FIG. 16 is an image of one example of the inlet or outlet die of FIG. 15 in a different view.

In some embodiments, one or more of the cutouts 706 may be sized to receive a wire 115 (FIG. 1), such as a pull wire, which may be provided by the wire handling system 107 (FIG. 1). In some embodiments, the interior cross-sectional shape of die 700 may be used in both the input die and the outlet die to accommodate the wires 115 pulled through the cutouts 706. For example, FIG. 16 shows a perspective view of one example of an inlet die 710 having the interior cross-sectional shape of the die 700.

Figure 17:
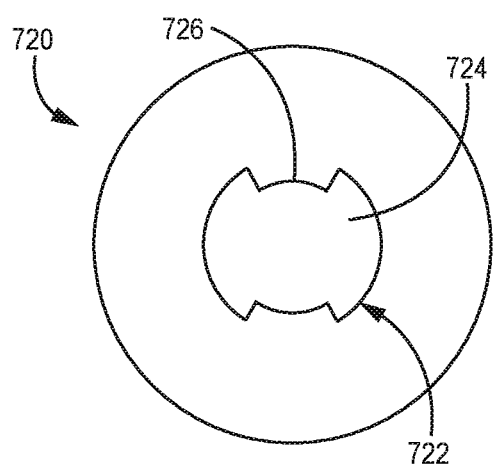
FIG. 17 is a conceptual diagram that illustrates another example of an inlet or outlet die that may be used, for example, in the heating cartridge in the additive manufacturing system of FIG. 1.

FIG. 17 shows an end view one example of an inlet or outlet die 720 that may be used in the heating cartridge 102 (FIG. 1). The die 720 may define a substrate inlet or outlet port 722. The port 722 may define a main region 724 and one, two, three, four, or more protrusions 726, or cutout regions. In the illustrated embodiment, the port 722 defines two protrusions 726, or teeth.

When the interior cross-sectional shape die 720 is used in an outlet die, the jacket formed by the heating cartridge 102 may include a number of channels corresponding to the number of protrusions 726 used in the die 720. For example, the illustrated die 720 would produce two channels on the jacket.

Figure 18:
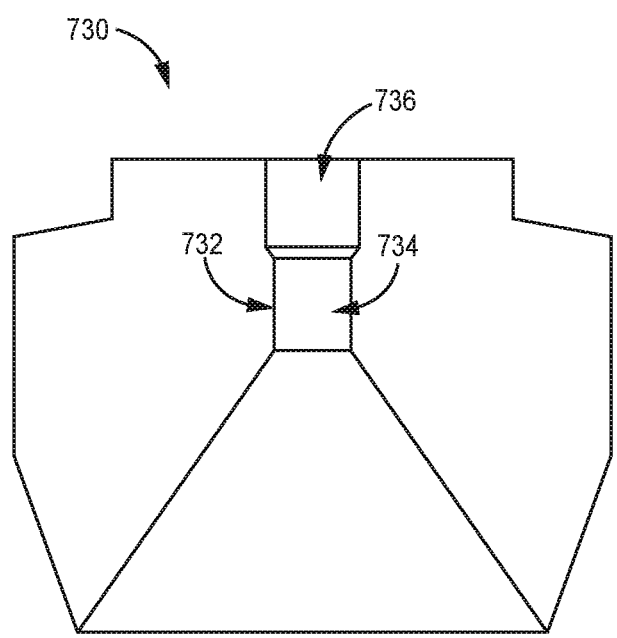
FIG. 18 is a conceptual diagram that illustrates an example of an outlet die that may be used, for example, in the heating cartridge in the additive manufacturing system of FIG. 1.

FIG. 18 shows a cross-sectional side view of one example of an outlet die 730 that may be used in the heating cartridge 102 (FIG. 1). The die 730 may define a substrate outlet port 732. The port 732 may define a proximal portion 734 and a distal portion 736. The distal portion 736 may have a width or diameter that is greater than the proximal portion 734. The distal portion 736 may be described as a relieved portion.

The change in diameter between the portions 734, 736 may define an interior shoulder or a shoulder on the interior surface.

The outlet die 730 may be used to change a thickness of the jacket. In some embodiments, the feeding force of the one or more filaments may be used to change the thickness of the jacket when used with the outlet die 730. In one example, a catheter jacket may have an outer diameter of 0.100 inches when running at a federate of F100 and an outer diameter of 0.110 when running at a federate of F175.

Figure 19:
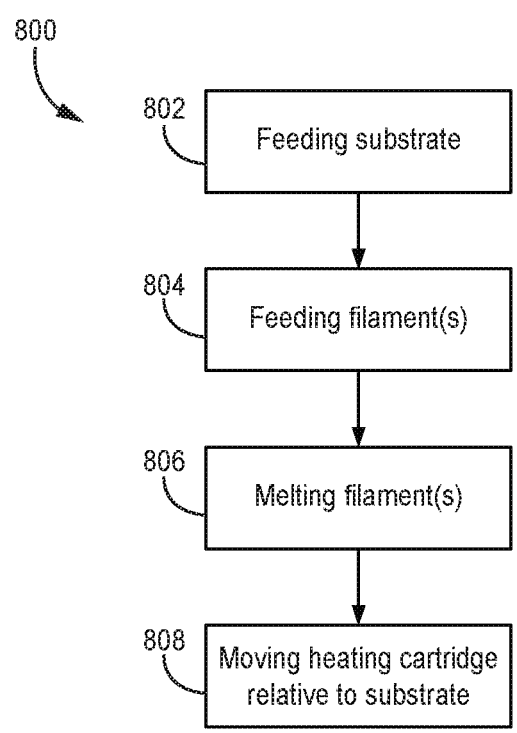
FIG. 19 is a flow diagram that illustrates one example of a method for use with, for example, the additive manufacturing system of FIG. 1.

FIG. 19 shows one example of a method 800 of using the system 100 (FIG. 1) for additive manufacturing. The method 800 may be used to manufacture an implantable medical catheter.

The method 800 may include feeding the substrate 802, for example, through a substrate channel in a heating cartridge. The substrate channel may be in fluid communication with an interior cavity of the heating cartridge.

The method 800 may include feeding one or more filaments 804. For example, at least a first filament may be fed through a filament port of the heating cartridge into the interior cavity. In some embodiments, a second filament may be fed through another filament port into the interior cavity.

The method 800 may include melting one or more of the filaments 806, for example, in the interior cavity. Any portion of the filaments contained in the interior cavity may be melted. In some embodiments, a second filament is melted with the first filament.

The method 800 may include moving the heating cartridge relative to the substrate 808, for example, at least in a longitudinal direction to form a catheter jacket comprising material from at least the first filament. The heating cartridge or substrate may also be rotated relative to one another. The catheter jacket may be formed from material of at least the first filament. In some embodiments, the catheter jacket may be formed from material of at least the first filament and the second filament.

In some embodiments, the method 800 may also include adjusting a ratio of the first filament relative to the second filament over a longitudinal distance to change the Shore durometer of the catheter jacket over the longitudinal distance.

Illustrative Embodiments

While the present disclosure is not so limited, an appreciation of various aspects of the disclosure will be gained through a discussion of the specific examples and illustrative embodiments provided below. Various modifications of the examples and illustrative embodiments, as well as additional embodiments of the disclosure, will become apparent herein.

A1. An additive manufacturing apparatus comprising:
a heating block at least partially defining an interior volume to allow an elongate substrate to pass through the interior volume and through the heating block, wherein the heating block at least partially defines a first filament port in fluid communication with the interior volume; and
a first guide sheath coupled to the heating block and extending into the first filament port from an exterior of the heating block, the first guide sheath defining a lumen in fluid communication with the interior volume.

A2. The apparatus according to embodiment A1, further comprising a support element coupled to the first guide sheath proximate to the heating block A3. The apparatus according to embodiment A2, wherein the support element is a thermal insulator A4. The apparatus according to embodiment A2 or A3, wherein the support element comprises a thermoplastic.

A5. The apparatus according to any one of embodiments A2 to A4, wherein the support element comprises polyamide-imide.

A6. The apparatus according to any one of embodiments A2 to A5, wherein the support element has a higher Shore durometer than the first guide sheath.

A7. The apparatus according to any one of embodiments A2 to A6, wherein a distal end of the support element and a distal end of the first guide sheath engage a first shoulder defined by the first filament port.

A8. The apparatus according to any one of embodiments A2 to A6, wherein a distal end of the support element engages a first shoulder defined by the first filament port and the a distal end of the first guide sheath engages a second shoulder defined by the first filament port distal to the first shoulder.

A9. The apparatus according to any preceding A embodiment, wherein a distal portion or distal end of the first guide sheath is proximate to or adjacent to the interior volume.

A10. The apparatus according to any preceding A embodiment, wherein the first guide sheath comprises a synthetic fluoropolymer.

A11. The apparatus according to any preceding A embodiment, wherein the first guide sheath comprises polytetrafluoroethylene.

A12. The apparatus according to any preceding A embodiment, further comprising an inlet die at least partially defining a substrate inlet port and an outlet die at least partially defining a substrate outlet port, wherein the interior volume is at least partially defined by the inlet die coupled to a proximal side of the heating block and at least partially defined by the outlet die coupled to the heating block at a distal side of the heating block.

A13. The apparatus according to embodiment A12, wherein one or both of the substrate inlet port and the substrate outlet port defines one, two, three, four, or more cutouts.

A14. The apparatus according to embodiment A13, wherein each cutout is configured to receive a pull wire.

A15. The apparatus according to any one of embodiments A12 to A14, wherein one or both of the substrate inlet port and the substrate outlet port defines one, two, three, four, or more protrusions.

A16. The apparatus according to any one of embodiments A12 to A15, wherein one or both of the inlet die and the outlet die comprises an interior shoulder.

A17. The apparatus according to any preceding A embodiment, wherein the heating block at least partially defines a second filament port in fluid communication with the interior volume.

A18. The apparatus according to embodiment A17, wherein a second guide sheath is coupled to a heat sink, the heat sink is coupled to a heat break, and the heat break at least partially extends into the second filament port and is coupled to the heating block.

A19. The apparatus according to any preceding A embodiment, further comprising one or more heating elements thermally coupled to the heating block to melt filament material in the interior volume.

B1. An additive manufacturing system comprising:
a heating cartridge extending from a proximal side to a distal side and comprising a substrate inlet port at the proximal side and a substrate outlet port at the distal side, the heating cartridge defining an interior volume and a substrate channel extending through the interior volume from the proximal side to the distal side, wherein the heating cartridge defines a first filament port in fluid communication with the interior volume to receive the first filament and a second filament port in fluid communication with the interior volume;

a heating element thermally coupled to the heating cartridge to heat the interior volume;

a filament handling system comprising one or more motors to feed at least a first filament through the first filament port and a second filament through the second filament port into the interior volume;

a substrate handling system comprising:
 a head stock comprising a distal clamp to secure a distal portion of an elongate substrate, wherein the substrate is positioned to pass through the substrate channel when secured by the head stock; and
 one or more motors to translate or rotate one or both of the substrate when secured by the headstock and the heating cartridge relative to one another; and a controller operably coupled to the heating element, one or more motors of the filament handling system, and one or more motors of the substrate handling system, the controller configured to:
 activate the heating element to melt any portion of the first filament or the second filament in the interior volume;
 control the one or more motors of the filament handling system to selectively control the feeding of the first filament and the second filament into the interior volume; and
 control one or more motors of the substrate handling system to move one or both of the substrate and the heating cartridge relative to one another in at least a longitudinal direction to form an elongate catheter jacket around the substrate, wherein the catheter jacket comprises material from at least one of the first filament and the second filament.

B2. The system according to embodiment B1, wherein the heating cartridge comprises a guide sheath extending into the first filament port, the guide sheath defining a lumen in fluid communication with the interior volume.

B3. The system according to embodiment B2, wherein the guide sheath extends between the filament handling system and the interior volume.

B4. The system according to embodiment B2 or B3, wherein a distal portion or distal end of the guide sheath is proximate to or adjacent to the interior volume.

B5. The system according to any one of embodiments B2 to B4, wherein the heating cartridge comprises a support element coupled to the guide sheath.

B6. The system according to any preceding B embodiment, wherein the first filament has a Shore durometer less than or equal to 90 A, 80 A, 70 A, 80 D, 72 D, 70 D, 60 D, 50 D, 40 D, or 35 D.

B7. The system according to any preceding B embodiment, wherein the first filament has a Shore durometer 10 D, 20 D, 30 D, 35 D, or 40 D less than a Shore durometer of the second filament.

B8. The system according to any preceding B embodiment, wherein the heating cartridge comprises an inlet die, a heating block, and an outlet die, wherein heating block defines the first filament port and the second filament port.

B9. The system according to any preceding B embodiment, further comprising a concentricity guide defining a channel spaced longitudinally from the heating cartridge positioned to engage the catheter jacket.

B10. The system according to embodiment B9, wherein the concentricity guide comprises an adjustable member to laterally position the catheter jacket relative to the channel of the concentricity guide.

B11. The system according to any preceding B embodiment, wherein the filament handling system comprises one, two, or more pinch rollers operably coupled to the one or more motors of the filament handling system to engage one or both of the first filament and the second filament.

B12. The system according to any preceding B embodiment, wherein one or both of the substrate inlet port and the substrate outlet port defines one, two, three, four, or more cutouts, and the controller is configured to rotate the substrate relative to the heating cartridge while translating the substrate relative to the heating cartridge to form the elongate catheter jacket around the substrate.

B13. The system according to embodiment B12, further comprising a wire handling system to provide a catheter pull wire to each of the cutouts.

B14. The system according to embodiment B12 or B13, wherein the substrate outlet port defines the one, two, three, four, or more cutouts and the catheter jacket comprises a number of helical protrusions corresponding to the number of cutouts.

B15. The system according to any preceding B embodiment, wherein one or both of the substrate inlet port and the substrate outlet port defines one, two, three, four, or more protrusions.

B16. The system according to embodiment B15, wherein the substrate outlet port includes the one, two, three, four, or more protrusions and the catheter jacket comprises a corresponding number of channels.

B17. The system according to any preceding B embodiment, wherein the substrate outlet port of the heating cartridge defines an interior shoulder, wherein the controller is configured to vary at least one of: a longitudinal speed of the substrate relative to the heating cartridge, a feeding force applied to at least one of the first filament and the second filament, and an amount of heat provided by the heating element to change a thickness of the catheter jacket over a longitudinal distance.

B18. The system according to any preceding B embodiment, wherein the controller is configured to change a feeding force applied to at least one of the first filament and the second filament to change a ratio of material in the catheter jacket over a longitudinal distance.

B19. The system according to embodiment B18, wherein the change in ratio of material in the catheter jacket over the longitudinal distance is continuous.

B20. The system according to any preceding B embodiment, wherein the controller is configured to move the head stock in at least the longitudinal direction away from the heating cartridge to form the catheter jacket.

B21. The system according to any preceding B embodiment, wherein the substrate handling system comprises a tail stock comprising a proximal clamp to secure a proximal portion of the substrate.

B22. The system according to embodiment B21, wherein the controller is configured to move the heating cartridge in at least the longitudinal direction away from the head stock to form the catheter jacket.

B23. The system according to any preceding B embodiment, further comprising the substrate, wherein the substrate comprises a lubricious coating, a liner, and a braid, and the catheter jacket is formed around the braid.

C1. A method for additive manufacturing of an implantable medical catheter, the method comprising:

feeding a substrate through a substrate channel in a heating cartridge, the substrate channel in fluid communication with an interior cavity of the heating cartridge;

feeding at least a first filament through a filament port into the interior cavity;

melting the first filament in the interior cavity; and moving the heating cartridge relative to the substrate at least in a longitudinal direction to form a catheter jacket comprising material from at least the first filament.

C2. The method according to embodiment C1, further comprising:

feeding a second filament through another filament port into the interior cavity; and melting the second filament with the first filament to form the catheter jacket comprising material from at least the first filament and the second filament C3. The method according to embodiment C2, further comprising adjusting a ratio of the first filament relative to the second filament over a longitudinal distance to change the Shore durometer of the catheter jacket over the longitudinal distance.

C4. The method according to any preceding C embodiment, wherein feeding the first filament through the filament port comprises feeding the first filament through a guide sheath extending into the filament port.

C5. The method according to embodiment C4, wherein a distal portion or distal end of the guide sheath is proximate to or adjacent to the interior volume.

C6. The method according embodiment C4 or C5, wherein feeding the first filament through the filament port comprises feeding the first filament through a support element coupled to the guide sheath.

C7. The method according to claim C6, wherein the support element has a higher Shore durometer than the guide sheath.

Thus, various embodiments of ADDITIVE MANUFACTURING FOR MEDICAL DEVICES are disclosed. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

As used herein, the term "configured to" may be used interchangeably with the terms "adapted to" or "structured to" unless the content of this disclosure clearly dictates otherwise.

Th singular forms "a," "an," and "the" encompass embodiments having plural referents unless its context clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

What is claimed:

1. An additive manufacturing apparatus comprising: a heating block at least partially defining an interior volume to allow an elongate substrate to pass through the interior volume and through the heating block, wherein the heating block at least partially defines a first filament port in fluid communication with the interior volume; and a first guide sheath coupled to the heating block and extending into the first filament port from an exterior of the heating block, the first guide sheath defining a lumen in fluid communication with the interior volume, wherein the heating block at least partially defines a second filament port in fluid communication with the interior volume separate from the first filament port.

2. The apparatus of claim 1, further comprising a support element coupled to the first guide sheath proximate to the heating block.

3. The apparatus of claim 2, wherein the support element is a thermal insulator.

4. The apparatus of claim 2, wherein the support element has a higher Shore durometer than the first guide sheath.

5. The apparatus of claim 2, wherein a distal end of the support element and a distal end of the first guide sheath engage a first shoulder defined by the first filament port.

6. The apparatus of claim 2, wherein a distal end of the support element engages a first shoulder defined by the first filament port and a distal end of the first guide sheath engages a second shoulder defined by the first filament port distal to the first shoulder.

7. The apparatus of claim 1, wherein a distal portion or distal end of the first guide sheath is proximate to or adjacent to the interior volume.

8. The apparatus of claim 1, further comprising an inlet die at least partially defining a substrate inlet port and an outlet die at least partially defining a substrate outlet port, wherein the interior volume is at least partially defined by the inlet die coupled to a proximal side of the heating block and at least partially defined by the outlet die coupled to the heating block at a distal side of the heating block.

9. The apparatus of claim 8, wherein one or both of the inlet die and the outlet die comprises an interior shoulder.

10. The apparatus of claim 1, wherein a second guide sheath is coupled to a heat sink, the heat sink is coupled to a heat break, and the heat break at least partially extends into the second filament port and is coupled to the heating block.

11. The apparatus of claim 1, further comprising one or more heating elements thermally coupled to the heating block to melt filament material in the interior volume.

12. An additive manufacturing system comprising:
a heating cartridge extending from a proximal side to a distal side and comprising a substrate inlet port at the proximal side and a substrate outlet port at the distal side, the heating cartridge defining an interior volume and a substrate channel extending through the interior volume from the proximal side to the distal side, wherein the heating cartridge defines a first filament port in fluid communication with the interior volume to receive the first filament and a second filament port in fluid communication with the interior volume;
a heating element thermally coupled to the heating cartridge to heat the interior volume;
a filament handling system comprising one or more filament handling motors to feed at least a first filament through the first filament port and a second filament through the second filament port into the interior volume;
a substrate handling system comprising:
a head stock comprising a distal clamp to secure a distal portion of an elongate substrate, wherein the substrate is positioned to pass through the substrate channel when secured by the head stock; and
one or more substrate handling motors to translate or rotate one or both of the substrate when secured by the headstock and the heating cartridge relative to one another; and
a controller operably coupled to the heating element, one or more filament handling motors, and one or more substrate handling motors, the controller configured to:
activate the heating element to melt any portion of the first filament or the second filament in the interior volume;
control the one or more filament handling motors to selectively control the feeding of the first filament and the second filament into the interior volume; and
control the one or more substrate handling motors to move one or both of the substrate and the heating cartridge relative to one another in at least a longitudinal direction to form an elongate catheter jacket around the substrate, wherein the catheter jacket comprises material from at least one of the first filament and the second filament.

13. The system of claim 12, wherein the heating cartridge comprises a guide sheath extending into the first filament port, the guide sheath defining a lumen in fluid communication with the interior volume.

14. The system of claim 13, wherein the guide sheath extends between the filament handling system and the interior volume.

15. The system of claim 13, wherein a distal portion or distal end of the guide sheath is proximate to or adjacent to the interior volume.

16. The system of claim 13, wherein the heating cartridge comprises a support element coupled to the guide sheath.

17. The system of claim 12, wherein the first filament has a Shore durometer less than or equal to 90 A, 80 A, 70 A, 80 D, 72 D, 70 D, 60 D, 50 D, 40 D, or 35 D.

18. The system of claim 12, wherein the first filament has a Shore durometer 10 D, 20 D, 30 D, 35 D, or 40 D less than a Shore durometer of the second filament.

19. The system of claim 12, wherein the heating cartridge comprises an inlet die, a heating block, and an outlet die, wherein heating block defines the first filament port and the second filament port.

20. The system of claim 12, further comprising a concentricity guide defining a channel spaced longitudinally from the heating cartridge positioned to engage the catheter jacket.

21. The system of claim 20, wherein the concentricity guide comprises an adjustable member to laterally position the catheter jacket relative to the channel of the concentricity guide.

22. The system of claim 12, wherein the substrate outlet port of the heating cartridge defines an interior shoulder, wherein the controller is configured to vary at least one of:
a longitudinal speed of the substrate relative to the heating cartridge, a feeding force applied to at least one of the first filament and the second filament, and an amount of heat provided by the heating element to change a thickness of the catheter jacket over a longitudinal distance.

23. The system of claim 12, wherein the controller is configured to change a feeding force applied to at least one of the first filament and the second filament to change a ratio of material in the catheter jacket over a longitudinal distance.

24. The system of claim 23, wherein the change in ratio of material in the catheter jacket over the longitudinal distance is continuous.

25. The system of claim 12, wherein the controller is configured to move the head stock in at least the longitudinal direction away from the heating cartridge to form the catheter jacket.

* * * * *